United States Patent [19]
Lee

[11] Patent Number: 5,174,281
[45] Date of Patent: Dec. 29, 1992

[54] BIRTH-ASSISTING PNEUMATIC CUFF

[75] Inventor: Ling H. Lee, Memphis, Tenn.

[73] Assignee: Wagi L.P., Memphis, Tenn.

[21] Appl. No.: 618,069

[22] Filed: Nov. 26, 1990

[51] Int. Cl.⁵ .................... A61B 17/42; A61H 1/00; A61H 31/00

[52] U.S. Cl. .................. 128/31; 128/24 R; 128/775; 128/30.2; 606/121; 606/119; 606/202

[58] Field of Search .............. 128/24 R, 24.2, 28, 128/30, 30.2, 31, 775, 778; 606/119, 121, 201, 202

[56] References Cited

U.S. PATENT DOCUMENTS

| | | | |
|---|---|---|---|
| 1,646,596 | 10/1927 | Mildenburg | 128/24 R |
| 2,597,637 | 5/1952 | Herdenwolf | 128/31 |
| 2,618,269 | 11/1952 | Baum et al. | 606/202 |
| 3,179,106 | 4/1965 | Meredith | 128/24 R |
| 3,520,294 | 7/1970 | Fuzzell et al. | 128/775 |
| 3,659,609 | 5/1972 | Arouete | 606/202 |
| 4,375,217 | 3/1983 | Arkani | 128/24 R |
| 4,624,248 | 11/1986 | Poole et al. | 606/201 |
| 4,865,020 | 9/1989 | Bullard | 128/24 R |
| 4,922,893 | 5/1990 | Wright et al. | 128/24 R |

FOREIGN PATENT DOCUMENTS

| | | | |
|---|---|---|---|
| 165879 | 5/1950 | Austria | 606/121 |
| 1225889 | 8/1987 | Canada | 128/28 |
| 327879 | 8/1989 | European Pat. Off. | 606/202 |
| 1800287 | 4/1970 | Fed. Rep. of Germany | 606/119 |
| 762285 | 4/1934 | France | 128/28 |
| 337982 | 6/1959 | Switzerland | 128/31 |

Primary Examiner—Richard J. Apley
Assistant Examiner—Karen G. Horowitz

[57] ABSTRACT

A pneumatic cuff assembly fitting over and around the entire maternal abdomen is intermittently inflated to a low and safe pressure in synchrony with the mother's voluntary straining efforts in order to augment the intra-abdominal pressure to assist the delivery of the fetus at the final stage of child birth.

4 Claims, 1 Drawing Sheet

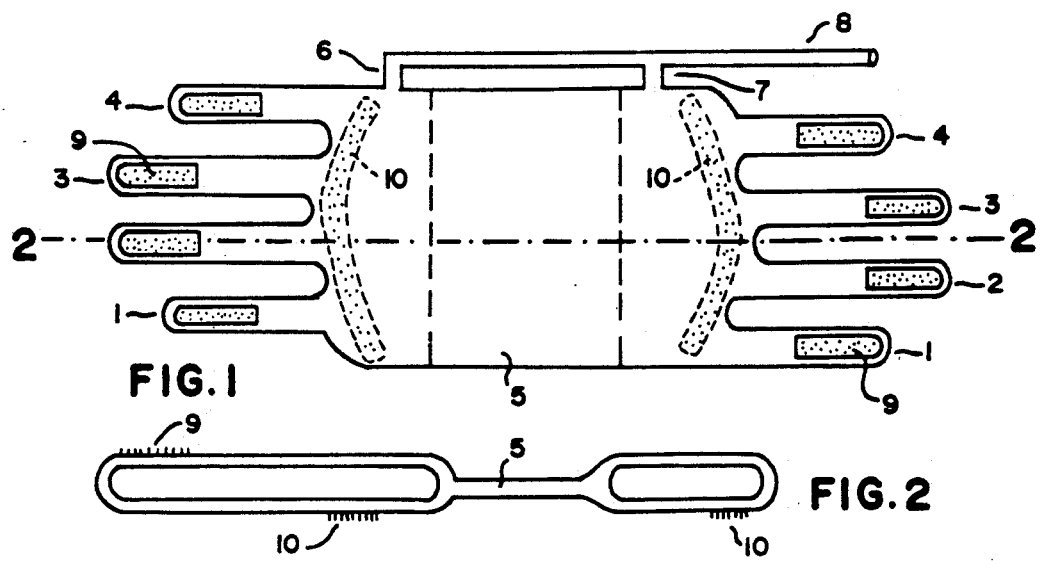
FIG. 1
FIG. 2
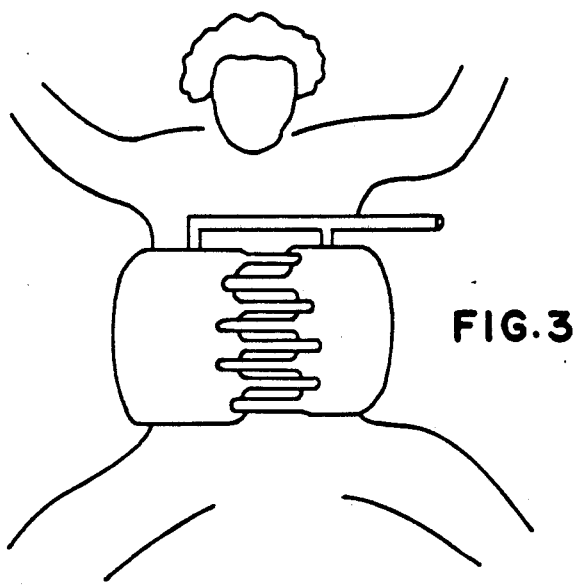
FIG. 3
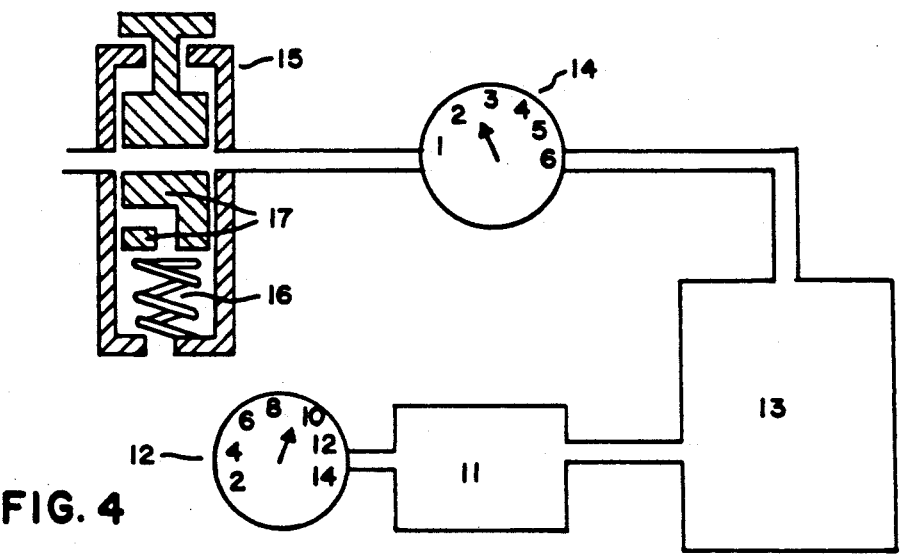
FIG. 4

BIRTH-ASSISTING PNEUMATIC CUFF

BACKGROUND OF THE INVENTION

1. Field of Invention

The field of invention concerns an obstertric device to augment the intra-abdominal pressure to assist child birth, more specifically a contour fitted double layer pneumatic cuff aound the material abdomen intermittently inflated at the final stage of child birth to assist the explusion of the fetus.

2. Description of Prior Art

For a century or more, physicians have used, when necessary and indicated, at the final stage of child brith, a pair of outlet forceps to pull the fetal head out of the birth canal. Improper timing, improper fitting, and excessive pulling sometimes to produce injuries to the fetal head or neck. A preliminary search of the U. S. patents classes/subclasses 127/78, 80. C, and 5/466 filed to reveal anything relevent or related to this instant invention.

SUMMARY OF THE INVENTION

During the early period of child-bearing labor, spontaneous and periodic contractions of uterine muscles produce gradual dilation of the ripened uterine cervix and push the fetus gradually down the birth canal. At the final stage, as the utrein contractions are more forceful and the cervix fully dilated, additional maternal voluntary straining spells come in to play. Anatomically and physiologically, straining is accomplished by voluntary contractiosn of the abdominal wall muscles while the larnyx is closed, thus increasing the intra-abdominal pressure, much like the effort of moving one's bowel. However, as often observed, the abdominal muscle contractions are weakened by hours of exhaustive labor, by medications, or by spinal anesthesia. The purpose of this invention is to use external and safe means to augment the intra-abdominal pressure at the final stage of child birth. Another objective of this invention is to reduce the need for outlet forceps which sometimes produce injuries to the fetal head and neck.

To accomplish the purposes, as will be further explained in the following description and further defined in the claims, a contour-fitted double layer pneumatic cuff around the entire maternal abdomen is inflated intermittently to a small and safe pressure in synchrony with each of the maternal straining effort. The cuff is deflated quickly as the maternal straining effort ceases.

DESCRIPTION OF THE DRAWINGS

FIG. 1 is a frontal view of the opened cuff.

FIG. 2 is a sectional view of FIG. 1 at the plane A—A.

FIG. 3 is a frontal view of the cuff having applied on a patient.

FIG. 4 is a diagram of the compressed air supply and the control valve.

DESCRIPTION OF THE PREFERRED EMBODIMENTS AND THE FUNCTION OF THE COMPONENT

In order to fit over the entire protuberant maternal abdomen, the configuration of the double layer pneumatic cuff can best be described as a pair of giant hand gloves with the middle "fingers" 2 and 3 longer than end "fingers" 1 and 4 and with the bases of the two "gloves" connecting to a third middle rectangular section 5 as depicted in FIG. 1 and FIG. 2. The middle rectangular section 5 on which the patient lies connecting the bases of two "gloves" has only one layer. Each of the two "gloves" has its own air hose connection 6 and 7, then to a common hose 8. When the entire cuff fits over the abdomen, as depicted in FIG. 3, the configuration is similar to a pair of opposing gloved hands with the right fingers interposing the left fingers. On the "palmar" side near the end of each of the finger leaf is mounted a strip of hook and loop material such as that sold under the trademark VELCRO 9 which meets a strip of the VELCRO mate 10 mounted at the "dorsal" side at the base of the opposing finger leaves, as depicted in FIG. 1 and FIG. 2.

Attention is now directed at FIG. 4 depicting the schematic of the air supply and controls. Air pump 11, regulated by the pump regulator 12, as apparent to those skilled in the art, supplies compressed air to the reservoir tank 13. At the outlet of the reservoir 13 is an adjustable pressure reducer/regulator 14, as apparent to those skilled in the art. Between the regulator 14 and the common hose 8 is a hand-operated inflate/deflate valve 15. By virtue of the loaded spring 16 inside the valve body and by virtue of the design of valve core 17 as depicted, the valve 15 permits inflation of the cuff when pressed or activated. When released or deactivated, the valve 15 permits deflation of the the cuff.

The operation of the entire assembly is as follows: The device is operated only under the supervision of a qualified physician or midwife and only to be applied on conscious and cooperative patients. Near the end of obstetric labor, the cuff is applied on the abdomen; parts are connected; and the reservoir tank pressurized (to a recommended pressure of twenty pounds per square inch). At the final stage of delivery and synchronous with the mother's voluntary straining, the cuff is inflated. When the voluntary strainign stops, the cuff is manually deflated quickly. The setting of the pressure reducer/regulator is to be determined by the physician or midwife. Two to four pounds per square inch seems appropriate. The amount of additional expelling force can be roughly estimated: at two pounds per square inch of cuff pressure which is considered low and safe, and at ten square inches of crosssectional area of a fetal head, the force is twenty pounds, which is more than that is safely applied with a pair of outlet forceps. Generally speaking, a pushing force is safer on the mother and the child then a pulling force.

My invention resides not in any one of these features per se, but rather in the particular combination of all of them herein disclosed and claimed and it is distinguished from prior art in this particular combination of all its structures for the function specified. Those skilled in the art will appreciate that the conception, upon which this disclosed is based, may readily utilize as a basis for designing of other structures, emthods, and systems for carrying out the several purposes of the present invention. It is important, therefore, that the claims be regarded as including such equivalent construction and obvious derivative insofar as they do not depart from the spirit and the scope of the present invention.

Having described the need, the construction and the operation of the assembly, I claim:

1. A double layer pneumatic cuff assembly fitting around the entire maternal abdomen to intermittently augment the intra-abdominal pressure in synchrony with the patient's voluntary straining efforts at the final stage of child birth, wherein said cuff comprsies three integrally connected and cooperatively functioning sections:
- a right and a left double layer inflatable section, each section having plurality of connecting elongated fingered leaf segments the middle leaf segments being longer than the end leaf segments; each said section having its own air supply hose; such that when the said two sections are applied on the abdomen the fingered leaves are interlaced;
- a middle rectangular section fitting under the patient's back connecting to the bases of the two aforementioned sections said middle section having only one layer.

2. An assembly as set forth in claim 1 wherein a hook and loop fastener means is positioned near the end of each of the said fingered leaf segments on the side facing the abdomen, and a mating hook and loop fastener means is positioned at the base of said fingered leaf segments on the side facing away from the abdomen.

3. An assembly as set forth in claim 1 includes a pressure regulated air supply.

4. An assembly as set forth in claim 1 includes a hand-operated inflate/deflate control valve between the said cuff and the air supply.

* * * * *